United States Patent
Bonnette et al.

(10) Patent No.: US 10,004,846 B2
(45) Date of Patent: Jun. 26, 2018

(54) DOUBLE ACTION INFUSION PUMP

(71) Applicant: BOSTON SCIENTIFIC LIMITED, Hamilton (BM)

(72) Inventors: Michael J. Bonnette, Minneapolis, MN (US); David B. Morris, Anoka, MN (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 220 days.

(21) Appl. No.: 14/822,871

(22) Filed: Aug. 10, 2015

(65) Prior Publication Data

US 2015/0343137 A1 Dec. 3, 2015

Related U.S. Application Data (63) Continuation of application No. 13/794,528, filed on Mar. 11, 2013, now Pat. No. 9,107,986.

(51) Int. Cl.
*A61M 5/142* (2006.01)
*A61M 5/00* (2006.01)
(Continued)

(52) U.S. Cl.
CPC .......... *A61M 5/1422* (2013.01); *A61M 5/007* (2013.01); *A61M 5/14212* (2013.01);
(Continued)

(58) Field of Classification Search
CPC .............. A61M 2206/22; A61M 5/007; A61M 5/14216; A61M 5/1422; A61M 5/1412;
(Continued)

(56) References Cited

U.S. PATENT DOCUMENTS 4,468,222 A    8/1984   Lundquist
4,715,959 A *  12/1987  Allan ...................... A61M 1/16
                                                    210/321.71
(Continued)

FOREIGN PATENT DOCUMENTS

DE    202011108638 U1    3/2013
EP         1634613 A1    3/2006
(Continued)

*Primary Examiner* — Andrew Gilbert
*Assistant Examiner* — Hamza Darb
(74) *Attorney, Agent, or Firm* — Seager, Tufte & Wickhem, LLP (57) ABSTRACT

An infusion system includes a double action infusion pump. The pump includes a cylinder and a reciprocating piston received within the cylinder, the reciprocating piston separating a first pump chamber from a second pump chamber of the cylinder. A reciprocating motor is coupled with the reciprocating piston, and the first and second pump chambers alternate between filling and evacuating conditions with reciprocation of the reciprocating piston through operation of the reciprocating motor, and the speed of reciprocation is varied to provide a continuous output of fluid between the first and second pump chambers. A fluid source and a catheter are optionally coupled with the double action infusion pump. The catheter includes one or more infusion ports near a catheter distal portion, and the one or more infusion ports receive and expel the continuous output of fluid from the double action infusion pump.

17 Claims, 6 Drawing Sheets

(51) Int. Cl.
*F04B 9/109* (2006.01)
*F04B 5/02* (2006.01)
*F04B 11/00* (2006.01)
*A61M 5/14* (2006.01)

(52) U.S. Cl.
CPC .......... *A61M 5/14216* (2013.01); *F04B 5/02* (2013.01); *F04B 9/1095* (2013.01); *F04B 11/0041* (2013.01); *A61M 2005/1403* (2013.01); *A61M 2206/22* (2013.01); *F04B 9/109* (2013.01)

(58) Field of Classification Search
CPC .......... A61M 5/1456; A61M 2205/106; A61M 1/30; A61M 2005/1403; A61M 5/3146; A61M 2005/1402
See application file for complete search history.

(56) References Cited

U.S. PATENT DOCUMENTS

| | | | |
|---|---|---|---|
| 4,902,276 A | 2/1990 | Zakko | |
| 5,076,769 A | 12/1991 | Shao | |
| 5,114,314 A * | 5/1992 | Fujimoto | F04B 11/0058 417/18 |
| 5,843,022 A | 12/1998 | Willard et al. | |
| 5,916,197 A | 6/1999 | Reilly et al. | |
| 6,158,967 A | 12/2000 | Dupré | |
| 6,197,000 B1 | 3/2001 | Reilly et al. | |
| 6,227,807 B1 | 5/2001 | Chase | |
| 7,842,010 B2 | 11/2010 | Bonnette et al. | |
| 7,935,077 B2 | 5/2011 | Thor et al. | |
| 8,303,538 B2 | 11/2012 | Bonnette et al. | |
| 2001/0051785 A1 | 12/2001 | Bonnette et al. | |
| 2008/0275393 A1 | 11/2008 | Bonnette et al. | |
| 2010/0204573 A1 | 8/2010 | Spohn et al. | |
| 2010/0312223 A1* | 12/2010 | Kozak | A61B 17/22 604/528 |
| 2011/0152908 A1 | 6/2011 | Morris et al. | |
| 2011/0300010 A1 | 12/2011 | Jarnagin et al. | |
| 2012/0076666 A1* | 3/2012 | Romain | F04B 5/02 417/42 |

FOREIGN PATENT DOCUMENTS

| | | |
|---|---|---|
| JP | 5944268 B2 | 7/2016 |
| WO | 9415099 A1 | 7/1994 |

* cited by examiner

DOUBLE ACTION INFUSION PUMP

CROSS-REFERENCE TO RELATED APPLICATIONS

This Application is a Continuation Application of U.S. application Ser. No. 13/794,528, filed Mar. 11, 2013, now U.S. Pat. No. 9,107,986, the entire content of which is incorporated herein by reference.

TECHNICAL HELD

This document pertains generally, but not by way of limitation, to infusion and contrast delivery systems.

BACKGROUND

Thrombectomy is a procedure for removing thrombus from the vasculature. Mechanical and fluid based systems are used to remove thrombus and accordingly open clogged or partially clogged vessels. With fluid based systems an infusion fluid including one or more of saline, lytics and the like is infused to a treatment area of a vessel with a catheter, for instance a thrombectomy catheter. The hydrodynamic force of the infusion fluid and optionally the characteristics of the lytics dislodge thrombus and accordingly open the vessel.

In one example, the infusion fluid is delivered to the thrombectomy catheter in a pulsed manner with a pump including a single piston. The piston is moved in a first direction to draw fluid into a cylinder, and then moved in a second direction to push the fluid out of the cylinder to a treatment feature of the thrombectomy catheter (e.g., an orifice). The pulses of fluid generated by the piston pump are then discontinuously applied through the treatment feature of the thrombectomy catheter to dislodge thrombus from the vessel wall. Optionally, the cylinder is prefilled with a fluid (e.g., contrast fluid or infusion fluid for thrombectomy) and the piston is driven in a single direction to gradually infuse the fluid. Upon full delivery of the fluid the cylinder must be refilled before operation is continued.

In another example a multi-cylinder pump including a plurality of corresponding pistons are coordinated to provide a continuous flow of infusion fluid. Stated another way, the plurality of pistons are operated out of sync with one another to ensure that as one of the cylinders is filling with infusion fluid another of the cylinders is providing infusion fluid output. A mechanism (e.g., a software algorithm, mechanical mechanism or the like) is used to coordinate the pistons in this manner.

Overview

The present inventors have recognized, among other things, that a problem to be solved can include providing a continuous flow of infusion fluid to a vessel (e.g., for thrombus removal, contrast injection or the like) with a single reciprocating piston. Multi-piston pumps, when the pistons are coordinated, are able to provide continuous flow. However, coordinating algorithms or mechanical linkages are needed to sync the pistons and provide a continuous flow of fluid. Additionally, multi-piston pumps have a large volume to accommodate the plurality of cylinders, pistons and operating mechanisms.

In an example, the present subject matter can provide a solution to this problem, such as by a double action infusion pump using a single piston to provide fluid flow during reciprocation of the piston in first and second directions. Each of first and second pump chambers within the cylinder are alternately filled and evacuated with movement of a single piston. By varying the speed of the piston reciprocation (e.g., having different speeds in an intermediate segment of the cylinder and near top and bottom zones of the cylinder) the double action piston pump provides a continuous output of infusion fluid. The continuous output from the pump is delivered to one or more infusion ports of a catheter in one example, and the double action infusion pump thereby provides a continuous infusion flow through the infusion ports. A single piston infusion pump with this arrangement is compact relative to multi-piston pumps and readily configured for installation within a larger infusion system already configured for use of a single action reciprocating piston pump.

Furthermore, by varying a speed of the reciprocating piston from one end of an intermediate segment of the cylinder to the ends of the top or bottom zones (e.g., immediately prior to reversing movement of the piston) the continuous output of the double action pump provides (or approaches) a static flow rate, and the continuous infusion flow from the one or more infusion ports similarly provides (or approaches) a static flow rate. In one example, the speed is varied in these regions between an initial piston speed that nearly matches the piston speed within the intermediate segment and a greater terminating speed near the ends of the top and bottom zones (e.g., at the end of the piston travel).

The present inventors have recognized, among other things, that a problem to be solved can include providing a continuous flow of infusion fluid to a vessel (e.g., for thrombus removal, contrast injection or the like) with a single reciprocating piston. Multi-piston pumps, when the pistons are coordinated, are able to provide continuous flow. However, coordinating algorithms or mechanical linkages are needed to sync the pistons and provide a continuous flow of fluid. Additionally, multi-piston pumps have a large volume to accommodate the plurality of cylinders, pistons and operating mechanisms.

Further still, an infusion system including the double action infusion provides a single piston pump configured to provide a continuous uninterrupted flow of infusion fluid to a treatment site. In one example, the infusion system provided herein is used as a contrast injector. In contrast to previous systems that use a single piston containing a reservoir of contrast fluid within the cylinder, the infusion system including the double action infusion pump is able to continuously deliver contrast fluid without refilling of the pump cylinder. Instead, the contrast fluid is refilled in a reservoir (e.g., fluid source) in communication with the double action infusion pump.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
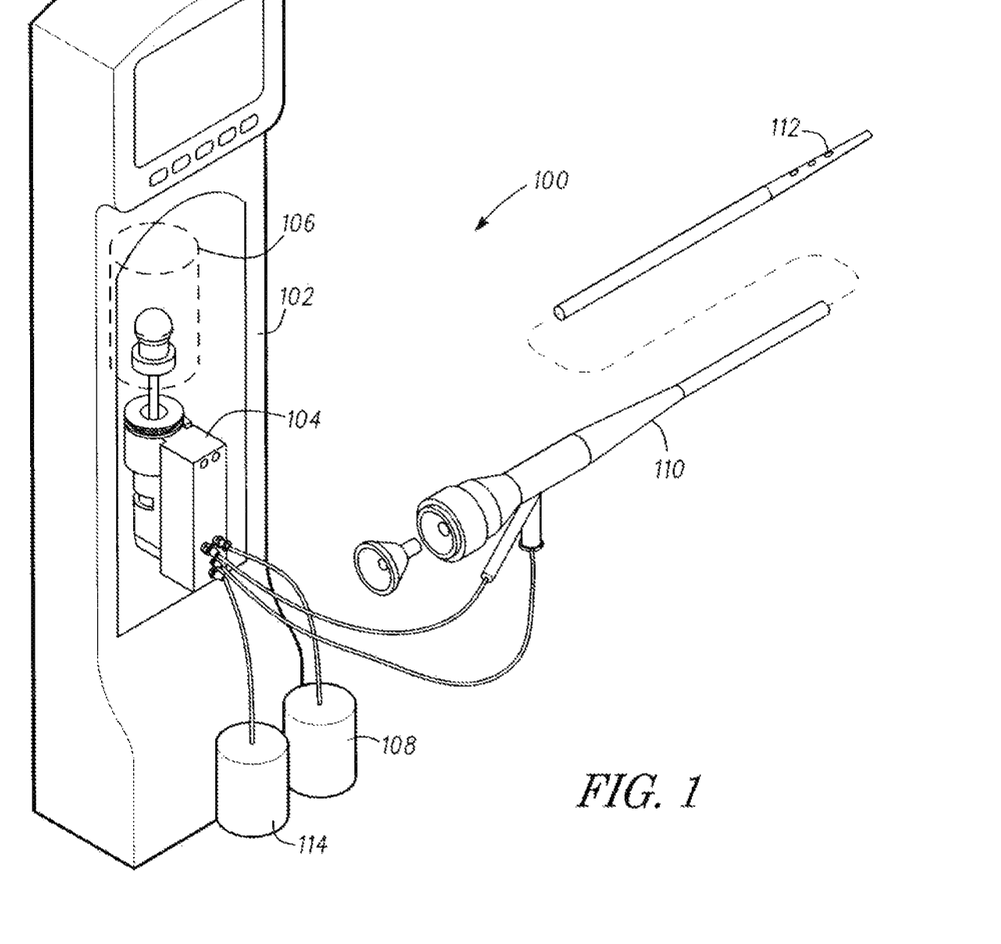
FIG. 1 is a schematic view of one example of an infusion system.

FIG. 1 is a schematic view of one example of an infusion system 100. The infusion system 100 includes a pump operator 102 coupled with a double action infusion pump 104. In the example shown in FIG. 1 the double action infusion pump is a reciprocating pump having a piston moving within a cylinder. The infusion system 100, for instance the pump operator 102, includes a pump motor 106 configured to couple with the piston of the double action infusion pump and accordingly reciprocate the piston within the cylinder of the double action infusion pump. As will be described herein the double action infusion pump 104 provides a continuous flow of fluid, for instance infusion fluid, to a catheter such as the catheter 110 shown in FIG. 1. The double action infusion pump 104 provides a continuous flow of fluid instance with reciprocation of the piston of the pump 104 by evacuating first and second pump chambers within the cylinder separated by the movable piston. The structure and operation of the double action infusion pump 104 will be described in further detail herein.

The output of the double action infusion pump 104 is in one example a substantially continuous output of fluid (e.g., saline, lytics or the like) provided to the catheter 110. In one example, the catheter 110 includes one or more infusion ports 112 shown in FIG. 1. The continuous output of fluid (e.g., with some fluctuation at the top and bottom of the piston travel) from the double action infusion pump 104 is correspondingly delivered to the infusion ports 112. Accordingly, a continuous flow of infusion fluid through the infusion ports 112 is provided (e.g., with some fluctuation from a steady state flow rate).

Figure 2:
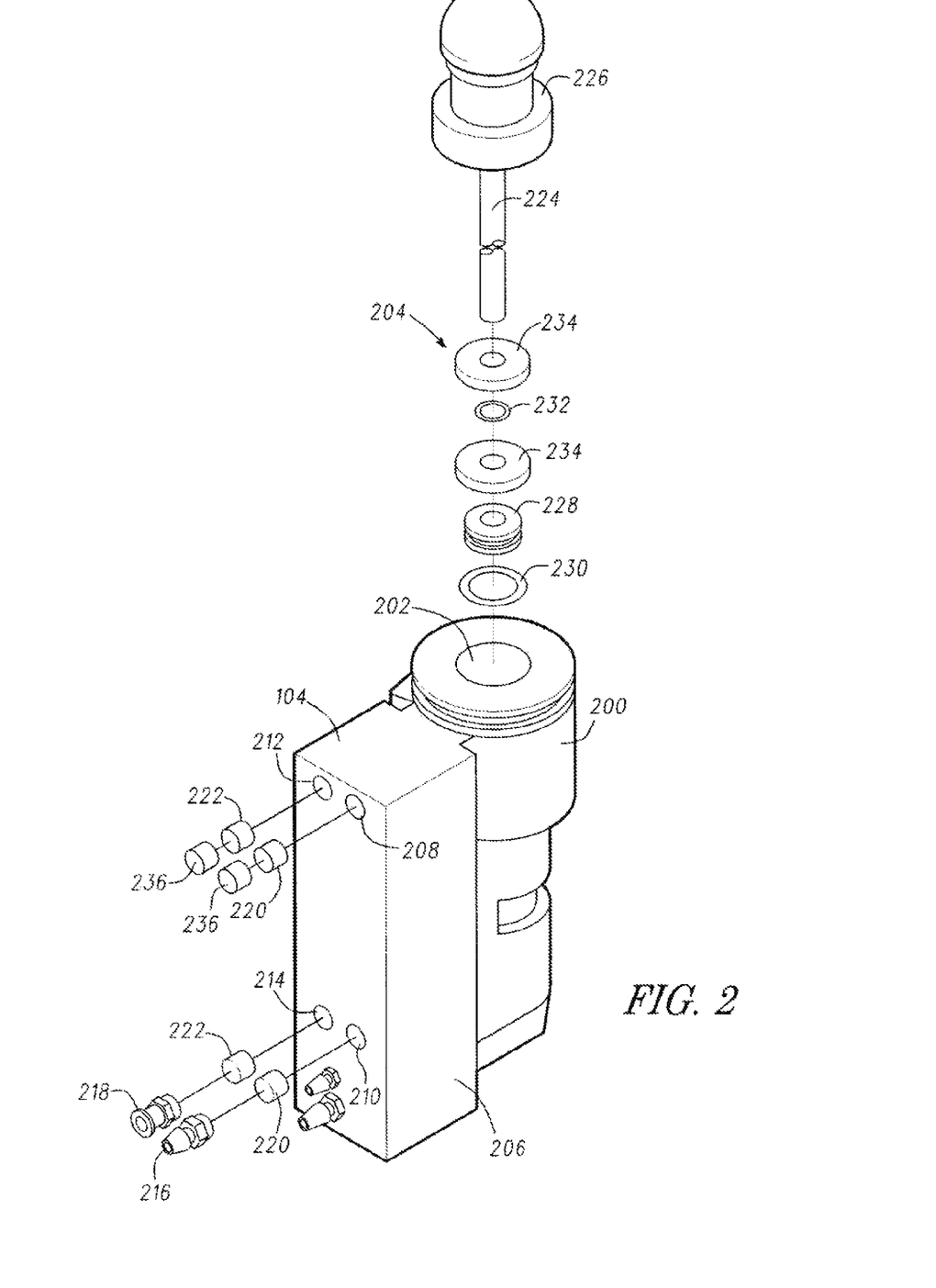
FIG. 2 is an exploded view of one example of a double action infusion pump.

Referring again to FIG. 1, in another example a fluid source 108 is coupled with the catheter 110. For instance the fluid source 108 is coupled with the double action infusion pump 104 and is delivered through the double action infusion pump 104 to infusion ports 112. The infusion system 100 includes an effluent reservoir 114 configured to receive an effluent provided by the catheter 110 (including in one example an entrained paniculate therein). In another example, for instance where the catheter 110 is a contrast injecting catheter, the infusion system 100 does not include the effluent reservoir or it is optional. Optionally, the double action infusion pump 104 is a unitary pump module having a unitary pump body including for instance one or more aspiration inlets and outlets configured to direct a flow of aspirated fluid (effluent) from the catheter 110 through a module including the double action infusion pump as well as the aspiration inlet and outlet fittings. As shown in FIG. 1, the effluent reservoir 114 is coupled with the double action infusion pump 104 and is accordingly in communication with the catheter 110, for instance an aspiration lumen extending through the catheter 110. FIG. 2 shows an exploded view of the double action infusion pump 104. As shown, the double action infusion pump 104 includes a pump body 200, for instance a unitary pump body formed from a single continuous piece of material. In the example, the cylinder 202 and the pump manifold 206 are formed as a single piece of material, for instance from a molded polymer resin. Where the double action infusion pump 104 is constructed with a polymer, in one example the cylinder 202 diameter and the corresponding piston 204 diameter are enlarged to provide a high flow rate at low pressures. Accordingly polymer fittings at the inlets and outlets, and the structural integrity of the cylinder 202 and the piston 204 are maintained while relatively high flow rates are realized. Optionally, the pump body 200 is machined from aluminum, steel or the like. Accordingly, the cylinder 202 and the corresponding inlets and outlets have increased structural integrity and the corresponding pump 104 is operable at higher pressures and corresponding flow rates, or at higher pressures with a smaller cylinder 202 and piston 204.

As further shown in FIG. 2, the double action infusion pump 104 includes a piston 204. In one example the piston 204 is a multicomponent piston including a series of seals configured to provide a sealing engagement between a piston disc 228 and the cylinder 202. The double action infusion pump 104 includes a series of inlets and outlets in communication with first and second pump chambers formed by the movable piston 204 and the cylinder 202. The contemporaneous evacuation and filling of each of these pump chambers accordingly provides a continuous output of infusion fluid for instance through a manifold outlet fitting 218 described in detail herein.

Referring again to FIG. 2, the piston 204 is shown in an exploded configuration. In the example shown the piston 204 includes a piston shaft 224 having a piston fitting 226. The piston fitting 226 is sized and shaped for engagement with a pump motor, such as the pump motor 106 shown in FIG. 1. The piston shaft 224 extends to a piston seat 234 sized and shaped to engage with a shaft seal 232 sized and shaped to maintain a fluid seal between the piston shaft 224 and at least the first pump chamber provided between the piston 204 and the piston seat 234. For instance, in one example a shaft seal 232 is sandwiched between dual portions of the piston seat 234 to accordingly provide a tight seal against the piston shaft 224 and accordingly prevent the egress of fluids from the cylinder 202. The piston shaft 224 is slidably received within the piston seat 234 and the shaft seal 232 and is coupled at an opposed end to the piston disc 228. In the example shown, the piston disc 228 includes a piston seal 230 sized and shaped to engage in sliding movement along the cylinder 202. The piston 204, including for instance the piston disc 228 and the piston seal 230, bifurcates the cylinder 202 into first and second pump chambers.

Referring again to FIG. 2 the cylinder 202 is in communication with a first fluid inlet 208 and a first fluid outlet 212 extending through the pump manifold 206. Similarly the second pump chamber (positioned relatively below the piston 204) is in communication with a second fluid outlet 214 and a second fluid inlet 210. The pump manifold 206 in another example includes a manifold inlet fitting 216 and a manifold outlet fitting 218. The manifold inlet fitting 216 is optionally in communication with the first fluid inlet 208 and the second fluid inlet 210. As will be shown for instance in FIG. 3, the manifold inlet fitting 216 is coupled with each of these fluid inlets 208, 210 to accordingly provide a source of fluid for each of the first and second pump chambers. In a similar manner, the manifold outlet fitting 218 is in communication with the first fluid outlet 212 and the second fluid outlet 214 associated with the first and second pump chambers, respectively. The manifold outlet fitting 218 is accordingly configured to couple with the catheter 110 shown in FIG. 1 and provide the continuous output of fluid flow from the pump 104 to the one or more infusion ports 112.

As further shown in FIG. 2 the double action infusion pump 104 includes a plurality of unidirectional valves provided in each of the inlets and outlets to accordingly ensure a unidirectional flow of fluid form each of the pump chambers. For instance, the first fluid inlet 208 includes a unidirectional inlet valve 220. In a similar manner, the second fluid inlet 210 includes a unidirectional inlet valve 220. The unidirectional inlet valves 220 (e.g., check valves) allow the inflow of fluid for instance into the cylinder 202 including the respective first and second pump chambers.

In a similar manner, the first and second fluid outlets 212, 214 correspondingly include unidirectional outlet valves 222. The unidirectional outlet valves 222 cooperate to ensure evacuating fluid from the cylinders 202 is delivered out of the first fluid outlet and the second fluid outlet 212, 214 and is not otherwise backflowed into the cylinder 202, for instance during reciprocation of the piston 204 while filling of either of the first and second piston chambers. Stated another way, the unidirectional inlet valves 220 and the unidirectional outlet valves 222 cooperate to provide a one way flow of fluid from each of the first and second pump chambers provided within the cylinder 202 and separated by the piston 204. Accordingly, through reciprocation of the piston 204 a flow of fluid is continuously provided from either of the first and second fluid outlets 212. 214 throughout reciprocation of the piston 204.

Optionally, the unidirectional inlet and outlet valves 220, 222 are reversed. In the the reversed configuration the double action infusion pump 104 is operable as a vacuum pump. For instance, in one example, the double action infusion pump 104 or a second instance of the pump is used as an aspiration pump to accordingly draw fluid (e.g., saline and body fluids with entrained particulate) to the effluent reservoir 114. Optionally, the pump in the vacuum configuration is coupled with the effluent reservoir-114 and applies a negative pressure within the reservoir to accordingly apply suction (e.g., to an aspiration lumen or catheter lumen of the catheter 110).

Figure 3:
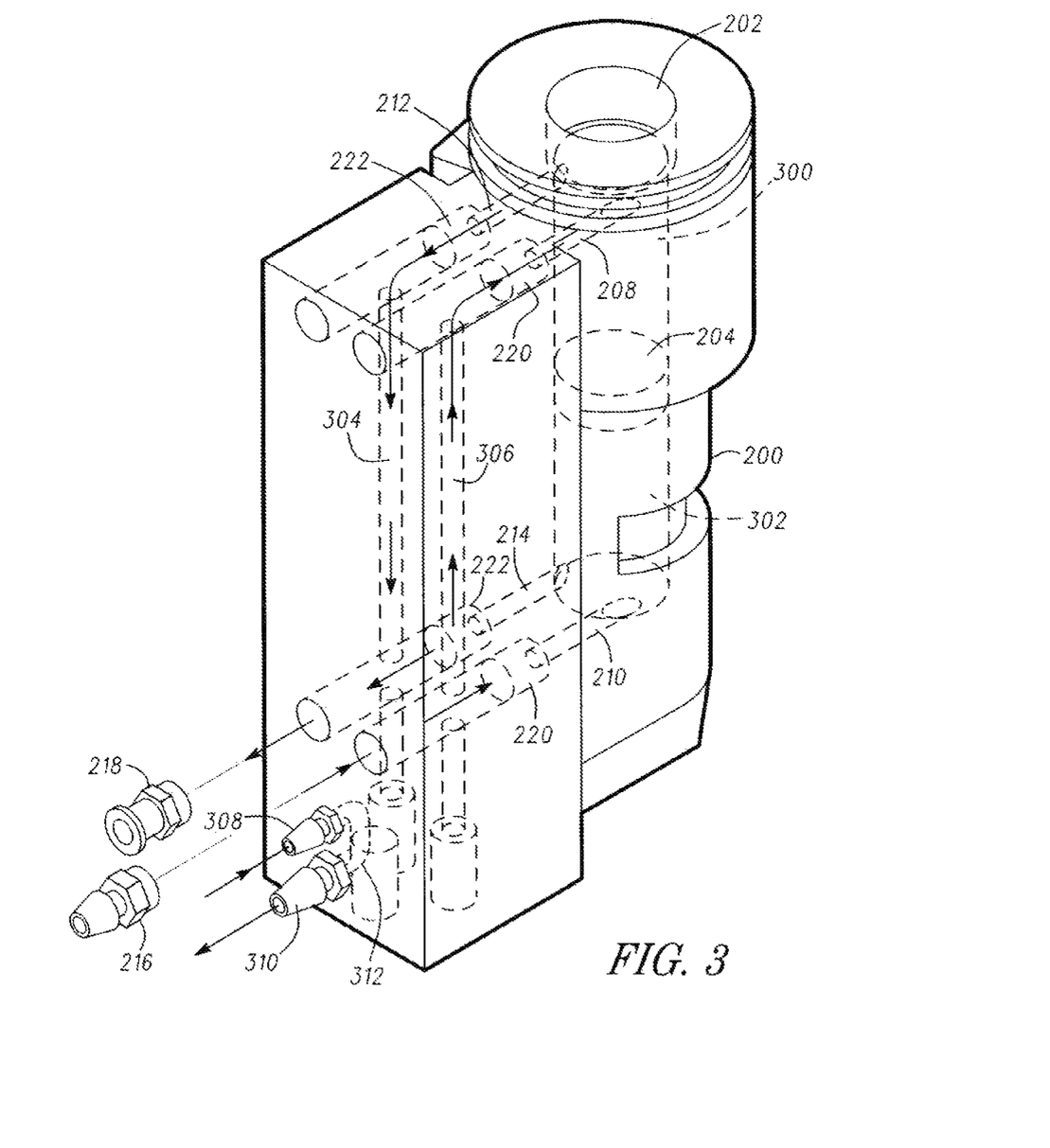
FIG. 3 is a cross sectional view of the double action infusion pump of FIG. 2.

FIG. 3 shows another perspective view of the double action infusion pump 104 previously shown in FIG. 2. In this view the interior of the infusion pump is provided in broken lines. For instance the cylinder 202 is shown divided by the piston 204 received therein. As shown in FIG. 3, the cylinder 202 is accordingly divided into a first pump chamber 300 and a second pump chamber 302. The first pump chamber 300 is in communication with the first and second fluid inlet and outlet 208, 212. In a similar manner, the second pump chamber 302 is in communication with the second fluid inlet and second fluid outlet 210, 214. As previously described each of the first fluid inlet and second fluid inlet 208, 210 are in one example in communication with a manifold inlet fitting 216. For instance, an inlet interconnect 306 formed within the pump manifold 206 provides communication between each of the first fluid inlet 208 and the second fluid inlet 210. In one example the manifold inlet fitting 216 is in communication with the fluid source 108 previously shown in FIG. 1.

In a similar manner to the first and second fluid inlets 208, 210, the first and second fluid outlets 212, 214 are in communication optionally with one another by way of an outlet interconnect 304. As shown in FIG. 3 each of the outlets 212, 214 are in communication by way of the interconnect 304 and accordingly provide their outputs through the manifold outlet fitting 218, for instance to the catheter 110 as shown in FIG. 1. In another example, each of the first and second fluid inlets 208, 210 and the first and second fluid outlets 212, 214 are respectively interconnected directly with a catheter such as the catheter 110. For instance the pump manifold 206 houses each of the inlets and outlets and accordingly allows for separate communication of each of the inlets and outlets with the corresponding catheter 110 or fluid source 108.

As further shown in FIG. 3 and as previously described herein, in one example the pump body 200 is a unitary pump body combining one or more features into a modular component assembly configured for installation within the pump operator 102 including the pump motor 106 shown in FIG. 1. That is to say, the double action infusion pump 104 including for instance a unitary pump body 200 is loaded as a single module into pump operator 102 and coupled with the catheter 110 as well as an effluent reservoir 114.

In one example, the pump operator 102 includes an aspiration pump such as a roller pump, a diaphragm pump or the like interposed between the effluent reservoir 114 and the double action infusion pump 104. The effluent pump provides a source of aspiration (e.g., a vacuum) within the catheter 110 and accordingly moves an effluent fluid (e.g., a returning fluid from the catheter 110 including for instance thrombus or plaque particulate therein) through the unitary pump body 200 and thereafter into the effluent reservoir 114. As shown in FIG. 3 in one example the pump body 200 in one example includes an aspiration inlet 308 and an aspiration outlet 310 formed in the pump body 200. As further shown in the figure an aspiration passage 312 provides communication between each of the aspiration inlet and the aspiration outlet 310. Accordingly, the aspiration inlet and outlet 308, 310 cooperate to provide an effluent passage through the pump body 200. The modular pump body 200 installed within the pump operator 102 accordingly facilitates communication from the fluid source 108 to the catheter 110 and from the catheter 110 to the effluent reservoir 114.

Figure 4A:
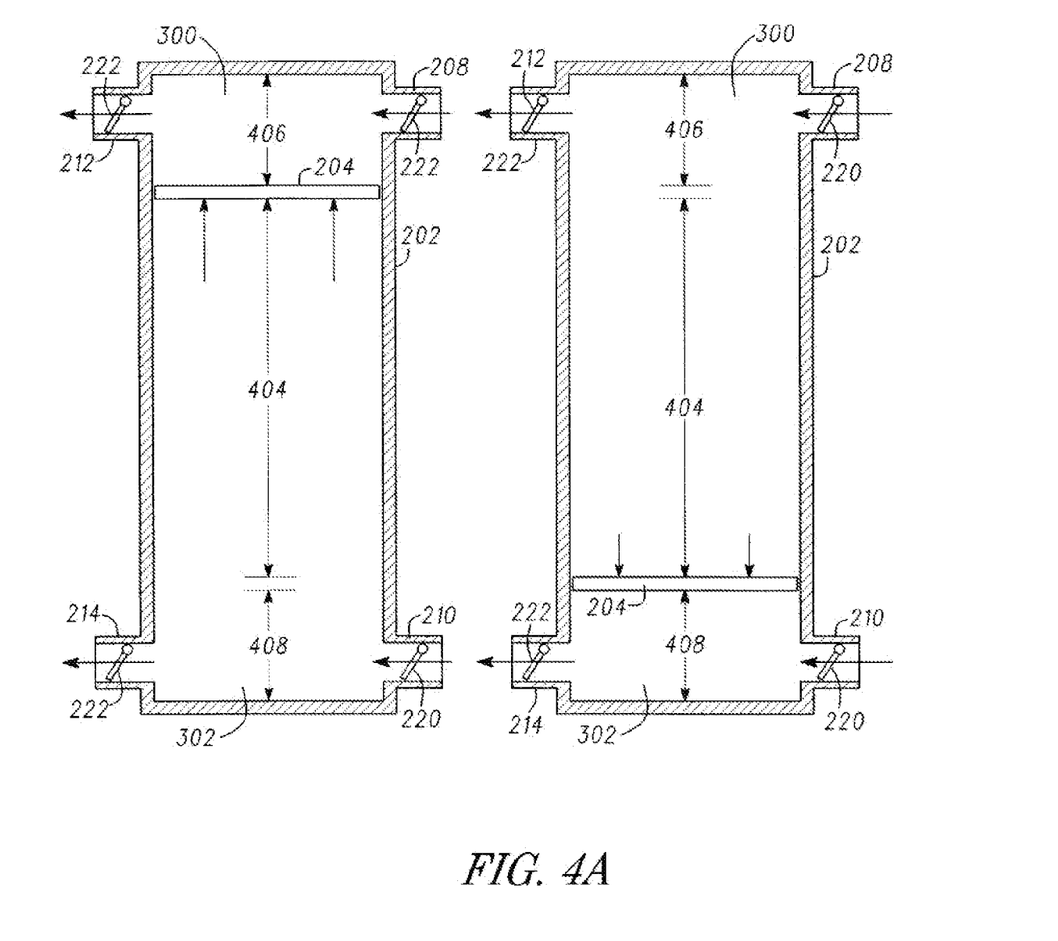
FIG. 4A is a schematic diagram showing a cylinder and piston of the double action infusion pump in two configurations.

Referring now to FIG. 4A the cylinder 202 previously shown in FIGS. 2 and 3 is shown in dual schematic representations with the piston 204 in an upward position in the leftmost view and the piston 204 in a lower position in the rightmost view. In both views the cylinder 202 includes first and second pump chambers 300, 302 formed by the piston 204 and the cylinder 202. As shown between the two views the first and second pump chambers 300, 302 have variable volumes according to the movements of the piston 204. The cylinder 202 includes first and second fluid inlets 208, 210 and first and second fluid outlets 212, 214. Each of the pairs of fluid inlets and outlets are associated with one of the first and second pump chambers 300, 302 as shown in each of the schematic views. As further shown in the schematic views each of the inlets and outlets include corresponding unidirectional inlet valves 220 and unidirectional outlet valves 222 such as check valves. Check valves facilitate in the example of the unidirectional inlet valve 220 filling of each of the respective first and second pump chambers 300, 302. In contrast the unidirectional outlet valves 222 associated with the first and second fluid outlets 212, 214 facilitate the evacuation of each of the first and second pump chambers 300, 302 for instance as the fluid within each of the chambers is pressurized during reciprocation of the piston 204.

In operation the piston 204 is reciprocated within the cylinder 202 to accordingly fill and evacuate each of the first and second pump chambers 300, 302. For instance, in the leftmost view the piston 204 is shown in an ascending configuration. In this configuration fluid within the first pump chamber 300 is pressurized and delivered through the first fluid outlet 212. In a converse manner, as the piston 204 ascends the second pump chamber 302 is filled for instance by a flow of fluid through the unidirectional inlet valve 220 of the second fluid inlet 210. Accordingly, as one of the first or second pump chambers 300, 302 is filling the opposed chamber is evacuating. The rightmost view of FIG. 4A shows the piston 204 in a descending configuration. In this configuration the first pump chamber 300 is filling for instance through the first fluid inlet 208 while the second pump chamber 302 is evacuating for instance by pushing pressurized fluid through the second fluid outlet 214.

According to the views shown in FIG. 4A a near continuous flow of fluid from the double action infusion pump 104 is provided, for instance as one of the first or second pump chambers 300, 302 is filling and the other is evacuating. Because one of the first and second pump chambers is evacuating during ascent or descent of the piston 204 a substantially continuous output is provided from the double action infusion pump (excepting a momentary pause at the top and bottom of the piston 204 travel). Similarly while one of the chambers is evacuating the other of the two chambers 300, 302 is filling to accordingly facilitate the continued delivery of fluid upon reciprocation of the piston 204 in the opposed direction.

Referring again to FIG. 4A the piston 204 is shown moving through various segments of the cylinder 202. In one example, an intermediate segment 404 spans a portion of the length of the cylinder 202 between top and bottom zones 406, 408. The intermediate segment 404 assumes the majority of the length of the cylinder 202 in an example. In another example, the intermediate segment 404 forms some portion of the cylinder 202 less than or equal to half of the cylinder length. As shown in FIG. 4A, the intermediate segment 404 spans between positions near the inlets and outlets 208, 210, 212, 214 but is spaced from the inlets and outlets relative to the top and bottom zones 406, 408 that are more closely positioned relative to the respective inlets and outlets.

As previously described the piston 204 is reciprocated. Stated another way, the piston 204 is moved in a first direction such as an ascending direction (the left view of FIG. 4A) to deliver pressurized fluid from the first pump chamber 300 for instance to a catheter such as the catheter 110 as shown in FIG. 1. Once the piston 204 is moved into an upward configuration for instance toward the end of the top zone 406 the piston 204 is reversed and moved in a second direction such as the descending configuration shown in the right view of FIG. 4A and eventually travels through the bottom zone 408. Accordingly, fluid within the second pump chamber 302 is pressurized and delivered through the second fluid outlet 214.

As the piston 204 reaches the top and bottom of its travel the piston experiences a momentary pause before it begins its reversed movement in the opposed direction. In one example, the double action infusion pump 104 described herein is configured to accelerate the movement of the piston 204 within each of the top and bottom zones 406, 408 relative to the intermediate segment 404 to attenuate the pause in the piston 204 and the according pause in delivery of fluid for instance from the first and second fluid outlets 212, 214. Stated another way, by accelerating the piston 204 in the top and bottom zones 406, 408 to a second speed greater relative to a first speed within the intermediate segment 404 the output from the first and second fluid outlets 212, 214 (e.g., a flow rate) is increased within the top and bottom zones 406, 408. Accordingly, a greater volume of fluid output from the double action infusion pump 104 is provided within the zones 406, 408 that allows for the maintenance of a substantially continuous output from the double action infusion pump 104 with only moderate variation in the overall output. The fluid flow delivered by catheter 110 for instance a contrast injecting catheter, thrombectomy catheter and the like is corresponding substantially continuous (e.g., having minor fluctuations) lagging behind the corresponding fluctuations in the substantially continuous output of the double action infusion pump 104.

In one example, the piston 204 within the intermediate segment 404 moves at a first piston speed, for instance a piston speed of around 0.01 inches to around 2 inches per second. At an interface between the top and bottom zones 406, 408 with the intermediate segment 404 the piston 204 accelerates or changes its speed to a second higher speed. The output of the double action infusion pump 104 correspondingly increases with the increased speed of the piston 204.

Optionally, as the piston 204 continues to ascend or descend within the respective top and bottom zones 406, 408 the speed within these zones is further increased for instance from an initial piston speed at the interface to a terminating piston speed near the end of each of the zones 406, 408. Accordingly, the fluid flow rate of the double action infusion pump at least within the top and bottom zones 406, 408 continues to rise as the piston 204 approaches the ends of the respective zones. In a similar manner, upon reaching the end of each of the zones the piston 204 reverses direction and begins moving again through the top or bottom zones 406, 408 toward the intermediate segment 404. Optionally the piston 204, while departing from the end of each of the top and bottom zones 406, 408, accelerates within the top and bottom zones 406, 408 to accordingly increase its output and maintain a near steady state constant volume of flow for the double action infusion pump 104. In still another example, the speed of the piston 204 on an upstroke (e.g., the leftmost view of FIG. 4A) is higher in one or more of the intermediate segment 204 or the top and bottom zones 406, 408 relative to the corresponding speeds of the downstroke to account for the change in volume caused by the piston shaft 224 (as shown in FIG. 2). Accordingly, by varying speed between the upstroke and downstroke a substantially continuous output of fluid from the pump 104 and flow of fluid at the catheter 110 are achieved.

Figure 4B:
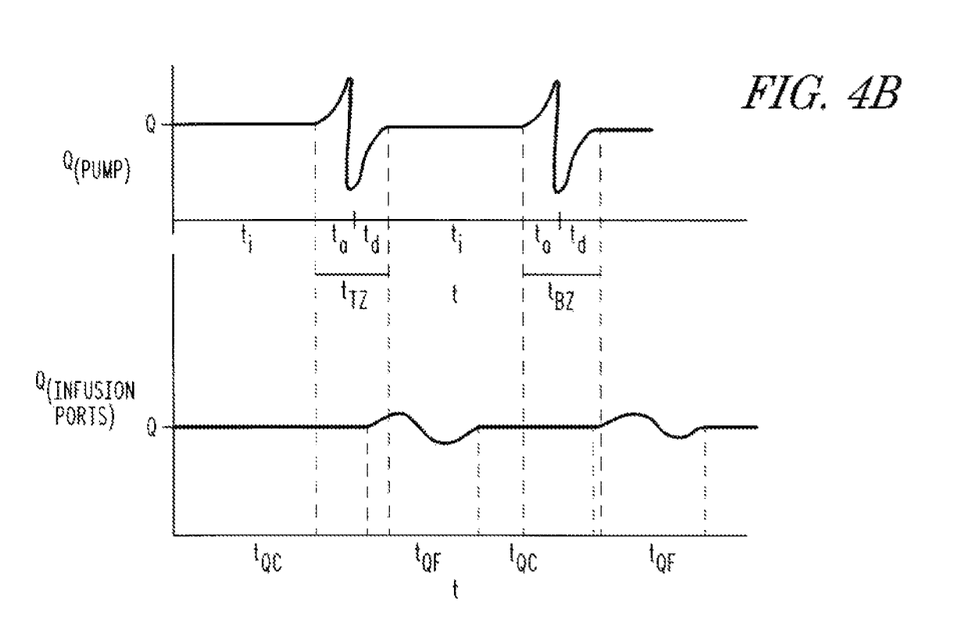
FIG. 4B is a diagram showing the respective continuous flow rates of the double action infusion pump and a catheter in communication with the double action infusion pump.

Referring to FIG. 4B, the output of the pump 104 for instance a value Q corresponding to the flow rate of the double action infusion pump 104 is plotted relative to a flow rate (Q of the infusion ports) corresponding to the output of a catheter, such as the catheter 110 shown in FIG. 1. As shown in the first plot corresponding to the flow rate of the pump 104 relative to time the flow rate of the pump is relatively constant through a time period corresponding to $t_j$ which is the time the piston 204 moves within the intermediate segment 404. As the piston moves into the top zone or bottom zone 406, 408 ($t_{TZ}$, $t_{BZ}$ respectively) and accordingly increases its speed the output of the pump accordingly rises (e.g., during a time of approach, time $t_a$). Upon reaching the end of either the top or bottom zones 406, 408 the piston pauses and then begins its descent or ascent (departs) from the top or bottom zones 406,408, respectively. As further shown in the first plot in FIG. 4B, the flow rate immediately rises toward the intermediate segment flow rate within the segment td (e.g., during a time of departure from the end of the top or bottoms zones 406, 408). By accelerating the piston 204 for instance raising its speed relative to a first speed within the intermediate segment 404 to a second speed in each of the top and bottom zones 406, 408 the overall output of the double action infusion pump 104 remains substantially constant, for instance rising and falling relative to a steady state output. Cessation of flow, for instance at the ends of the piston travel 204 is attenuated by way of accelerating the piston 204 within the top and bottom zones 406, 408.

Referring again to FIG. 4B the output of the one or more infusion ports 112 (the flow rate Q) is shown plotted relative to the output of the pump in the upper view. As shown the output of the infusion ports 112 lags slightly behind the output of the pump according to drag within the catheter 110 and the catheter length from the double action infusion pump 104 to the ports 112. As shown, with the substantial continuity of the pump output shown in the first view the corresponding fluid flow at the infusion ports 112 is substantially constant with only slight fluctuation around the stead state flow rate within a time period ($T_{QF}$). In the remainder of the plot of the flow rate the flow rate at the infusion ports 112 is substantially constant ($T_{QC}$).

Accordingly as shown in FIGS. 4A and 4B, by alternating filling and evacuating of each of the first and second pump chambers 300, 302 while at the same time varying the speed of the piston 204 a continuous output of fluid is provided by the double action infusion pump 104 (with slight fluctuations in the flow rate for instance corresponding to the top and bottom zones 406, 408) and a continuous flow of fluid at the one or more infusion ports 112 of the is provided (with some attenuated fluctuations corresponding to the changes in speed and the reversal of movement to the piston 204 as shown in FIG. 4A). That is to say, by changing the speed of the piston 204 the output of the double action infusion pump 104 described herein is made substantially continuous. Correspondingly, the output of the catheter 112 for instance a flow of fluid from the infusion ports 112 is also substantially continuous. Stated another way, the substantially continuous output of the double action infusion pump 104 and the catheter 110 have slight variations relative to a steady state flow rate but are otherwise continuous during the reciprocation of the piston 204 within the cylinder 202.

Figure 5:
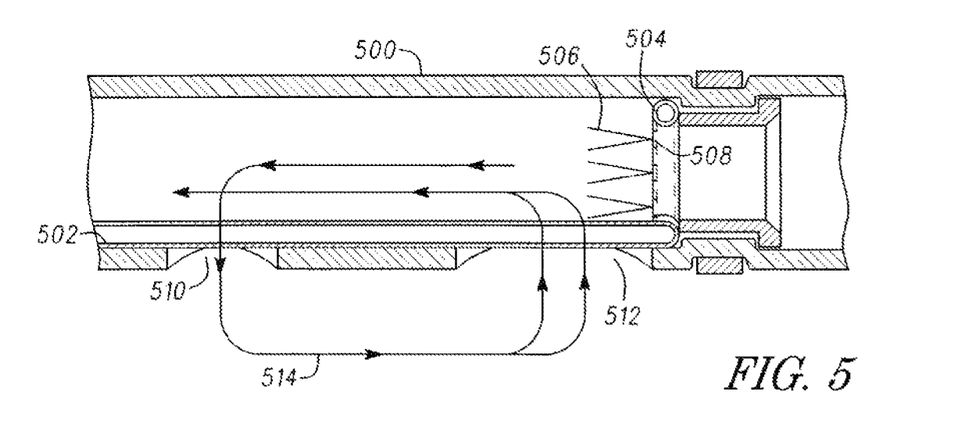
FIG. 5 is a cross sectional view of one example of a catheter distal portion of a thrombectomy catheter.

Referring now to FIG. 5 one example of a catheter, such as a distal portion 500 of the catheter 110 shown in FIG. 1 is provided. In this example the catheter 110 includes an emanator 504 positioned within the distal portion 500 of the catheter. The emanator 504 includes a plurality of infusion ports 508 arranged around a ring like structure of the emanator 504. An infusion tube such as the infusion tube 502 shown in FIG. 5 is in communication with the emanator 504 and delivers a pressurized fluid such as saline, lytics or the like to the infusion ports 508. Accordingly, one or more fluid jets 506 are formed within the catheter 110 and directed proximally for instance back toward the pump operator 102 shown in FIG. 1. The fluid jets 506 are configured to provide a proximal flow of fluid within the catheter distal portion 500. As shown in FIG. 5, the proximal flow generates a recirculating flow 514 of the fluid. For instance the distal portion of the catheter 500 includes an outflow orifice 510 and an inflow orifice 512 in communication with the flow of the fluid jets 506. The pressurized fluid jets 506 create an exterior flow of fluid through the outflow orifice 510 that allows the infused fluid to entrain particulate, such as thrombus or the like, therein and return the fluid with the entrained particulate through the outflow orifice 512 for maceration of the particulate and delivery of the particulate along the catheter 110, for instance to an effluent reservoir such as the reservoir 114 shown in FIG. 1.

In one example, the continuous output of the double action infusion pump 104 is provided by way of the infusion tube 502 to the emanator 504 to accordingly generate the fluid jets 506 and the corresponding recirculating flow 514. As previously described, the continuous output of the double action infusion pump 104 results in a corresponding continuous flow of fluid through the emanator 504 by way of the infusion tube 502. Accordingly, the recirculating flow 514 and the fluid jets 506 are substantially continuous and thereby able to generate a continuous recirculating flow 514 to ensure the reliable hydrodynamic-based removal of thrombus and particulate maceration, and further ensure continuous delivery of the entrained particulate to the effluent reservoir 114 provided in FIG. 1.

In another example, the distal portion 500 of the catheter includes direct spray infusion orifices in contrast to the recirculating flow provided with the inflow and outflow orifices 512, 510. Stated another way, the infusion tube 502 extends to the distal portion 500 and communicates with one or more infusion ports (e.g., the infusion ports 112 shown in FIG. 1). Alternatively, the infusion tube 502 communicates with an emanator like the ring type emanator shown in FIG. 5. The emanator includes peripheral infusion orifices directed through the catheter sidewall and to the exterior of the catheter. Accordingly, the emanator delivers streams or sprays of infusion fluid directly to the vasculature (e.g., thrombus within the vasculature).

Figure 6:
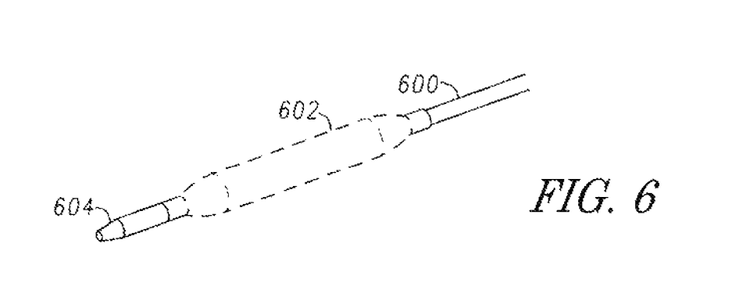
FIG. 6 is a perspective view of one example of a catheter distal portion of a contrast injecting catheter.

FIG. 6 shows another example of a distal portion 600 of a catheter, for instance in a contrast injecting catheter. As shown in the example, the distal portion 600 of the catheter includes an optional dilating balloon 602 sized and shaped to inflate within a vessel and accordingly occlude the vessel to facilitate the delivery of contrast fluid to a location of interest. The distal portion of the catheter 600 includes at least one infusion port 604, such as a contrast injecting port sized and shaped to provide a flow of contrast fluid distal to the dilating balloon 602. For instance, as previously described herein the infusion port 604 is in communication with the double action infusion pump 104. The continuous output of the double action infusion pump 104 is delivered along the catheter to the contrast infusing port 604 to accordingly deliver a contrast fluid in a continuous manner (e.g., with a continuous flow of fluid) to a location to be observed. Optionally, the infusion port is provided as a relatively large orifice, for instance within a delivery sheath or relatively large diameter catheter to accordingly facilitate delivery of the relatively viscous contrast fluid. In another example, the distal portion 600 of the catheter includes an infusion port 604 without a dilating balloon 602.

With the double action infusion pump 104 described herein, with reciprocation of a single piston such as the piston 204 shown in FIGS. 2 and 3 the pump 104 is able to generate, respectively, a substantially continuous output of fluid and substantially continuous flow of fluid from the pump and a catheter 110 coupled with the pump. Stated another way, with only minor fluctuations of an otherwise constant or static flow rate the double action infusion pump 104 is able by way of a single piston and cylinder combination 204,202 to provide a continuous flow of fluid at one or more infusion ports 112 associated with the catheter 110 (e.g., the infusion ports 508 or the infusion port 604).

Figure 7:
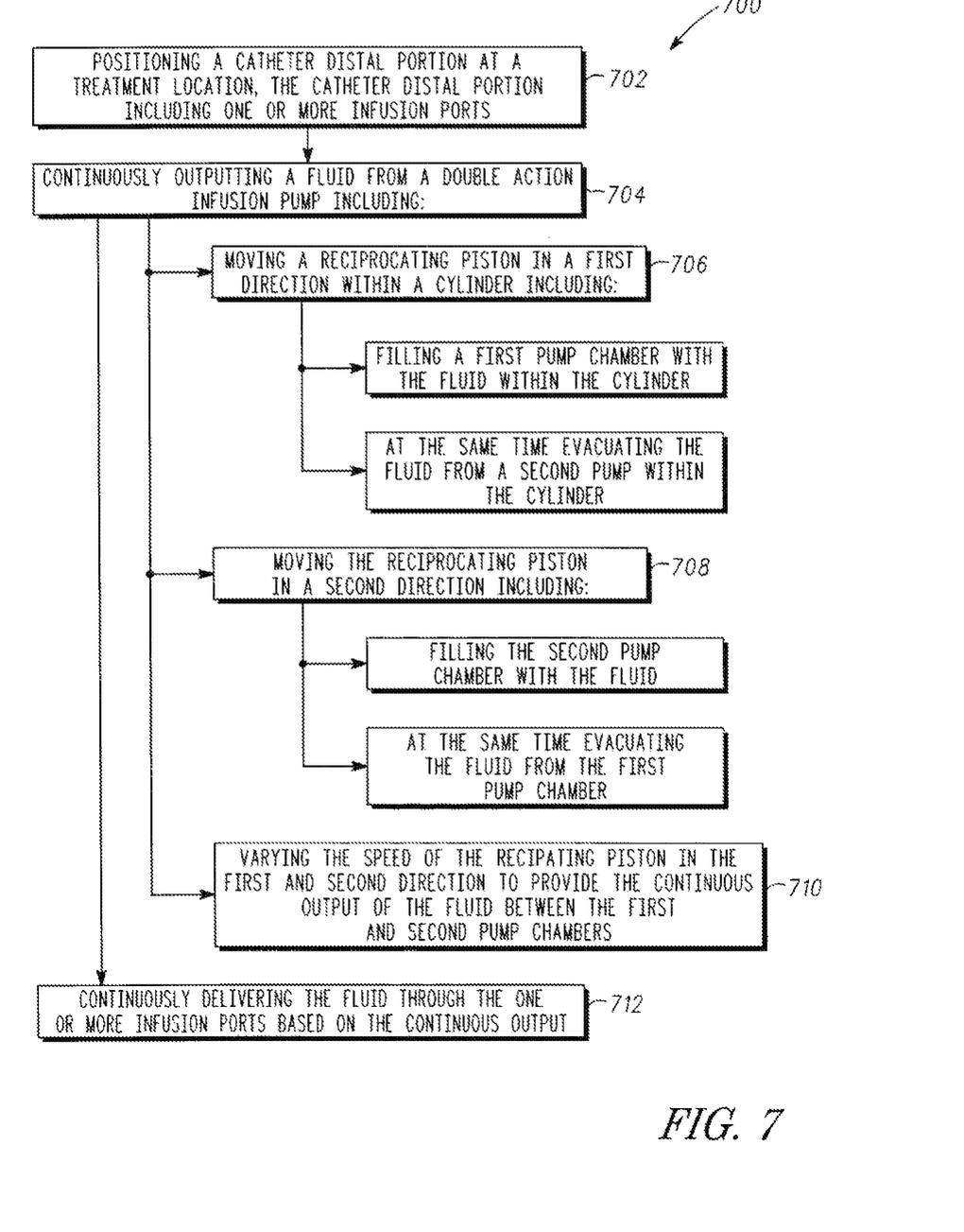
FIG. 7 is a block diagram showing one example of a method of infusing a fluid into a vessel.

FIG. 7 shows one example of a method 700 of infusing a fluid into a vessel. In describing the method 700 reference is made to one or more components, features, steps and the like described herein. Where convenient reference is made to the components, features and the like with reference numerals. The reference numerals provided are exemplary and are not exclusive, for instance the features, components and the like described in the method 700 include but are not limited to the corresponding numbered elements, other corresponding features described herein (both numbered and unnumbered) as well as their equivalents.

At 702, a catheter such as a catheter 110 shown in FIG. 1 having a catheter distal (e.g., either of the catheter distal portions 500, 600 shown in FIGS. 5 and 6) is positioned at a treatment location within the vessel. The catheter distal portion (500 or 600) includes one or more infusion ports (e.g., the infusion ports 508 and 604). As shown in FIGS. 5 and 6 in one example the catheter 110 shown in FIG. 1 includes a thrombectomy catheter configured to provided a recirculating flow of fluid 514 through an outflow orifice 510 and an inflow orifice 512 as shown in FIG. 5. The catheter 110 includes in another example, a contrast injecting catheter including for instance the catheter distal portion 600 shown in FIG. 6. In one example the contrast injecting catheter includes a dilating balloon 602 as well as an infusion port 604 sized and shaped to deliver a contrast fluid distally relative to the dilated balloon 602.

At 704, the method includes continuously outputting a fluid from a double action infusion pump 104 in communication with a fluid source 108, such as a source of contrast fluid, infusion fluid (saline, lytics)) or the like. Continuously outputting the fluid includes moving the reciprocating piston 204 in a first direction within a cylinder such as the cylinder 202 and moving the reciprocating piston in a second opposed direction within the cylinder 202. In one example, moving the reciprocating piston includes filling a first pump chamber 300 with the fluid within the cylinder while at the same time evacuating the fluid for instance another volume of the fluid from a second pump chamber 302 also within the cylinder 202 (see the rightmost view of FIG. 4A). Accordingly, while the first pump chamber 300 is filling the second pump chamber 302 with the piston 204 moving in the first direction is accordingly evacuating to provide a first portion of flow to the catheter 110 as shown in FIG. 1.

At 708, moving the reciprocating piston in a second direction such as an opposed direction (including for instance the leftmost view of FIG. 4A) includes filling the second pump chamber 302 with the fluid for instance the fluid provided by the fluid source 108 shown in FIG. 1. At the same time the first pump chamber 300 is evacuated, for instance by the piston 204 collapsing the first pump chamber 300 and accordingly delivering fluid from one of the two fluid outlets 212, 222 as shown in FIG. 4A. Accordingly, and in a similar manner to reciprocation of the piston in the first direction, reciprocation of the piston 204 in the second direction correspondingly fills the second pump chamber as the first pump chamber is evacuated. With reciprocation of the piston in the first and second directions a substantially continuous output of fluid is provided.

At 710 the method 700 further includes varying the speed of the reciprocating piston 204 in the first and second directions to provide the continuous output of the fluid between the first and second pump chambers 300, 302. That is to say, in one example the piston 404 is moved along an intermediate segment 404 of the cylinder 202 at a first piston speed, for instance a piston speed of between about 0.01 inches to 2 inches per second. As the piston 204 enters the top and bottom zones 406, 408 the piston is accelerated and its speed is increased to a second piston speed greater than the first piston speed to accordingly increase the flow rate of the double action infusion pump 104 within the corresponding top and bottom zones 406, 408. As previously described herein, by increasing the flow rate of the double action fusion pump 104 within each of the top and bottom zones 406, 408 (by raising the speed of the piston 204 within these zones) the output of fluid from the double action infusion pump 104 is continuous. That is to say, while there is some fluctuation near the top and bottom zones 406, 408 in the overall output of fluid, the output is substantially continuous as the piston 204 is accelerated toward the top and bottom zones 406, 408 (an optionally while departing from the top and bottom zones 406, 408) to increase the overall flow rate and thereby offset any decrease in flow rate otherwise provided by the pause of the piston 204 at the top and bottom of its movement.

At 712 fluid is continuously delivered through the one or more infusion points 112 of the catheter 110 based on the continuous output from the double action infusion pump 104. Referring to FIG. 4B, as shown with the flow rate of the pump 104 shown in the first plot adjusted according to the variations in speed of the piston 204 the corresponding output or fluid flow from the catheter infusion ports 112 is shown in the bottom plot. With the change in speed within the top and bottom zones 406, 408 the output of the double action infusion pump 104 increases in these zones to substantially realize an overall continuous output of fluid that offsets the decrease in output with the pause of reciprocation of the piston 204. Accordingly, the output of the catheter 110 for instance with the infusion ports 112 is substantially continuous and any fluctuations in the output from the double action infusion pump 104 are attenuated by drag in the catheter and connecting tubing and dispersion of the fluid within the catheter 110 to accordingly provide a substantially continuous flow rate with only minor variations (lagging those variations in the pump output).

Several options for the method 700 follow. In one example, filling of the first and second pump chambers 300, 302 with the fluid includes delivering fluid through respective first and second fluid inlets 208, 210 to the first and second pump chambers 300, 302 respectively. The first and second fluid inlets each include a unidirectional valve 220 as previously described herein. In a contrast, evacuating the fluid from the first and second pump chambers 300, 302 includes delivering fluid through the outlets 212, 214. In one example the first and second fluid outlets each include unidirectional outlet valves 222 as previously shown in FIGS. 2 and 4A.

In another example, varying the speed of the reciprocating piston 204 includes varying the speed between an intermediate segment 404 of the cylinder 202 and within top and bottom zones 406, 408 of the cylinder 202. Varying of the speed includes in one example moving the reciprocating piston 204 at a first piston speed along the intermediate segment 404 and moving the reciprocating piston 204 at a second piston speed greater than the first piston speed within the top and bottom zones 406, 408. Optionally, moving the reciprocating piston 204 at the second speed, for instance within the top and bottom zones 406, 408, includes moving the reciprocating piston 204 near an interface between the intermediate segment 404 and each of the top and bottom zones 406, 408 at an initial piston greater than the first piston speed within the intermediate segment 404. Additionally moving the reciprocating piston near ends of the top and bottom zones 406, 408 (adjacent to the end of the travel of the piston 204 in each of the reciprocating directions) includes moving at a terminating piston speed greater than the initial piston speed within the top and bottom zones 406, 408. Stated another way, the piston 204 optionally accelerates (or assumes 2 or more speeds) from between the interface between the top and bottom zones 406, 408 to the end of it travel within each of the top and bottom zones 406, 408.

In another example continuously delivering the fluid through the one or more infusion ports 112 includes continuously delivering a contrast fluid through one or more infusion ports such as the infusion port 604 shown in FIG. 6 with the contrast injecting catheter distal portion 600 shown in FIG. 6. In another example, continuously delivering the fluid through the one or more infusion ports includes generating the recirculating fluid loop such as the fluid loop 514 shown in FIG. 5. Generating the recirculating fluid loop 514 includes in one example continuously delivering the fluid through a fluid jet emanator 504 within a catheter lumen of the catheter such as the catheter distal portion 500 shown in FIG. 5. A portion of the continuously delivered fluid is provided through an outflow orifice 510 of the catheter in communication with the catheter lumen. The portion of the fluid delivered through the outflow orifice is returned through an inflow orifice 512 (with entrained paniculate therein). The inflow orifice communicates with the catheter lumen and the plurality of fluid jets 506 provided by the emanator 504.

In still another example, the method 700 further includes filling a fluid source such as the fluid source 108 while continuously outputting the fluid from the double action infusion pump 104 at the same time. That is to say, the double action infusion pump 104 may be operated continuously without needing to reload the cylinder or other feature of a pump to accordingly provide a renewed flow of fluid. Instead, the fluid source 108 provides an open ended supply of fluid to the double action infusion pump 104. Accordingly, with continued refilling of the fluid source 108 as needed the double action infusion pump 104 is able to continuously output a flow of fluid from the pump 104 and accordingly provide a continuous flow of fluid from the catheter 110, for instance chronically or near chronically positioned within a patient.

Various Notes & Examples

Example 1 can include subject matter such as an infusion system that can include a fluid source; a double action infusion pump in communication with the fluid source, the double action infusion pump including: a cylinder, a reciprocating piston received within the cylinder, the reciprocating piston separating a first pump chamber from a second pump chamber of the cylinder, each of the first and second pump chambers having a variable volume, a reciprocating motor coupled with the reciprocating piston, and the first and second pump chambers alternate between filling and evacuating conditions with reciprocation of the reciprocating piston through operation of the reciprocating motor, and the speed of reciprocation is varied to provide a continuous output of fluid between the first and second pump chambers; and a catheter coupled with the double action infusion pump, the catheter including one or more infusion ports near a catheter distal portion, and the one or more infusion ports receive and expel the continuous output of fluid from the double action infusion pump.

Example 2 can include, or can optionally be combined with the subject matter of Example 1, to optionally include wherein the fluid source is coupled with the first and second pump chambers with first and second fluid inlets, respectively, and the catheter is coupled with the first and second pump chambers with first and second fluid outlets, respectively.

Example 3 can include, or can optionally be combined with the subject matter of one or any combination of Examples 1 or 2 to optionally include wherein the first and second fluid inlets include unidirectional valves therein configured to allow inflow into the respective first and second pump chambers, and the first and second fluid outlets include unidirectional valves therein configured to allow outflow from the respective first and second pump chambers.

Example 4 can include, or can optionally be combined with the subject matter of one or any combination of Examples 1 through 3 to optionally include wherein the piston is reciprocated along an intermediate segment of the cylinder and through top and bottom zones, and along the intermediate segment of the cylinder the reciprocating motor moves the piston at a first piston speed, and within the top and bottom zones the reciprocating motor moves the piston at a second piston speed greater than the first piston speed.

Example 5 can include, or can optionally be combined with the subject matter of one or any combination of Examples 1-4 to optionally include wherein the reciprocating motor moves the piston at the first and second piston speeds to provide the continuous output of fluid received and expelled by the infusion ports.

Example 6 can include, or can optionally be combined with the subject matter of Examples 1-5 to optionally include wherein the second piston speed includes a plurality of speeds including an initial piston speed and a terminating piston speed, and an initial piston speed near an interface of each of the top and bottom zones within the intermediate segment is greater than the first piston speed in the intermediate segment, and a terminating piston speed near ends of the top and bottom zones is greater than the initial piston speed.

Example 7 can include, or can optionally be combined with the subject matter of Examples 1-6 to optionally include wherein the catheter includes a contrast infusion catheter, and the continuous flow of fluid from the catheter is a continuous flow of contrast fluid.

Example 8 can include, or can optionally be combined with the subject matter of Examples 1-7 to optionally include wherein the catheter includes a fluid jet emanator within a catheter lumen, and the one or more infusion ports include at least one outflow orifice in a catheter side wall in communication with the fluid jet emanator, and the catheter includes at least one inflow orifice in communication with the fluid jet emanator, and wherein the continuous flow of fluid is directed through the fluid jet emanator according to the continuous output of fluid between the first and second pump chambers, the continuous flow of fluid from the fluid jet emanator configured to generate a recirculating fluid loop through the inflow and outflow orifices between a catheter lumen and a catheter exterior.

Example 9 can include, or can optionally be combined with the subject matter of Examples 1-8 to optionally include an infusion system comprising a fluid source; a catheter including one or more infusion ports near a catheter distal portion; and a double action infusion pump in communication with the fluid source and the catheter, the double action infusion pump including: a cylinder, a reciprocating piston received within the cylinder, the reciprocating piston separating a first pump chamber from a second pump chamber of the cylinder, a first fluid inlet and first fluid outlet coupled with the first pump chamber, a second fluid inlet and second fluid outlet coupled with the second pump chamber, each of the first fluid inlet and outlet and the second fluid inlet and outlet includes a unidirectional valve therein, and wherein the first and second fluid inlets are in communication with the fluid source, and the first and second fluid outlets are in communication with the one or more infusion portions of the catheter.

Example 10 can include, or can optionally be combined with the subject matter of Examples 1-9 to optionally include a unitary pump body, and each of the cylinder, the first fluid inlet and outlet, and the second fluid inlet and outlet are formed from the unitary pump body, and the unitary pump body is configured for modular loading within a pump operator including a reciprocating motor, and the reciprocating motor is configured for engagement with the piston.

Example 11 can include, or can optionally be combined with the subject matter of Examples 1-10 to optionally include wherein the unitary pump body includes an aspiration interface, the aspiration interface including: an aspiration inlet configured for coupling with a catheter lumen of the catheter, and an aspiration outlet in communication with the aspiration inlet, the aspiration outlet configured for coupling with an effluent reservoir.

Example 12 can include, or can optionally be combined with the subject matter of Examples 1-11 to optionally include wherein the double action infusion pump is operated in an intermediate configuration and a dead center configuration, in the intermediate configuration the piston is moved at a first piston speed within an intermediate segment of the cylinder between top and bottom zones of the cylinder, and in the top and bottom configuration the piston is moved at a second piston speed within the top and bottom zones.

Example 13 can include, or can optionally be combined with the subject matter of Examples 1-12 to optionally include wherein operation of the double action infusion pump in the intermediate and the top and bottom configurations is configured to generate a continuous output of fluid between the first and second pump chambers and a corresponding continuous flow of fluid from the catheter.

Example 14 can include, or can optionally be combined with the subject matter of Examples 1-13 to optionally include wherein the catheter includes a contrast infusion catheter, and the continuous flow of fluid from the catheter is a continuous flow of contrast fluid.

Example 15 can include, or can optionally be combined with the subject matter of Examples 1-14 to optionally include a method of infusing a fluid into a vessel comprising: positioning a catheter distal portion at a treatment location, the catheter distal portion including one or more infusion ports; continuously outputting a fluid from a double action infusion pump in communication with a fluid source, continuously outputting including: moving a reciprocating piston in a first direction within a cylinder including filling a first pump chamber within the cylinder with the fluid, and at the same time evacuating the fluid from a second pump chamber within the cylinder, moving the reciprocating piston in a second direction including filling the second pump chamber with the fluid, and at the same time evacuating the fluid from the first pump chamber, and varying the speed of the reciprocating piston in the first and second directions to provide the continuous output of the fluid between the first and second pump chambers; and continuously delivering the fluid through the one or more infusion ports based on the continuous output from the double action infusion pump.

Example 16 can include, or can optionally be combined with the subject matter of Examples 1-15 to optionally include wherein filling the first and second pump chambers with the fluid includes delivering fluid through respective first and second fluid inlets to the first and second pump chambers, the first and second fluid inlets each including a unidirectional valve.

Example 17 can include, or can optionally be combined with the subject matter of Examples 1-16 to optionally include wherein evacuating the fluid from the first and second pump chambers includes delivering fluid through respective first and second fluid outlets from the first and second pump chambers, the first and second fluid outlets each including a unidirectional valve.

Example 18 can include, or can optionally be combined with the subject matter of Examples 1-17 to optionally include wherein varying the speed of the reciprocating piston includes varying the speed between an intermediate segment of the cylinder and within top and bottom zones of the cylinder including: moving the reciprocating piston at a first piston speed along the intermediate segment, and moving the reciprocating piston at a second piston speed greater than the first piston speed within the top and bottom zones.

Example 19 can include, or can optionally be combined with the subject matter of Examples 1-18 to optionally include wherein moving the reciprocating piston at the second piston speed includes: moving the reciprocating piston near an interface between the intermediate segment and each of the top and bottom zones includes moving at an initial piston speed greater than the first piston speed in the intermediate segment, and moving the reciprocating piston near ends of the top and bottom zones includes moving at a terminating piston speed greater than the initial piston speed.

Example 20 can include, or can optionally be combined with the subject matter of Examples 1-19 to optionally include wherein continuously delivering the fluid through the one or more infusion ports includes continuously delivering a contrast fluid through the one or more infusion ports.

Example 21 can include, or can optionally be combined with the subject matter of Examples 1-20 to optionally include wherein continuously delivering the fluid through the one or more infusion ports includes generating a recirculating fluid loop including: continuously delivering the fluid through a fluid jet emanator within a catheter lumen of the catheter, delivering a portion of the continuously delivered fluid through an outflow orifice of the catheter in communication with the catheter lumen, returning the portion of the continuously delivered fluid through an inflow orifice of the catheter in communication with the catheter lumen, and entraining paniculate within the returned portion of the continuously delivered fluid.

Example 22 can include, or can optionally be combined with the subject matter of Examples 1-21 to optionally include filling a fluid source while continuously outputting the fluid from the double action infusion pump.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-machine-readable medium encoded with instructions operable to configure an electronic device to perform methods as described in the above examples. An implementation of such methods can include code, such as microcode, assembly language code, a higher-higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An infusion system, comprising:
   an infusion pump including a chamber and a piston disposed within the chamber, the chamber having a first section including a first end, a second section including a second end, and a transition section positioned between the first section and the second section; and
   a catheter coupled to the infusion pump;
   wherein the piston moves through the first section at a first speed, the second section at a second speed, and the transition section at a third speed;
   wherein the piston changes direction at the first end of the chamber;
   wherein the first, the second or both the first and second speeds are greater than the third speed;
   and wherein the piston accelerates from the transition section as the piston approaches the first end of the chamber;
   wherein the piston has a first acceleration from the third speed to the first speed, and wherein the piston has a second acceleration from the third speed to the second speed, and wherein the first acceleration and the second acceleration are configured to provide a constant output of fluid out of the pump.

2. The infusion system of claim 1, wherein the first, second and third speeds are configured to provide a constant output of fluid out of the pump.

3. The infusion system of claim 1, wherein the first, second and third piston speeds correspond to a first output of fluid out of the pump, a second output of fluid out of the pump and a third output of fluid out of the pump, and wherein the first output, the second output or both the first and second outputs are greater than the third output.

4. The infusion system of claim 1, wherein the first, second and third speeds are variable, and wherein the piston adjusts the first, second and/or third speeds in response to an output of fluid out of the pump.

5. The infusion system of claim 1, wherein a movement of the piston causes a filling of the first section with fluid while simultaneously evacuating fluid from the second section.

6. The infusion system of claim 1, wherein the piston separates the first section from the second section.

7. The infusion system of claim 1, further comprising at least one inlet coupled to the first section, and at least one inlet coupled to the second section.

8. The infusion system of claim 7, wherein the transition section spans a distance between the at least one inlet coupled to the first section and the at least one inlet coupled to the second section.

9. The infusion system of claim 8, wherein the at least one inlet coupled to the first section and the at least one inlet coupled to the second section include at least one unidirectional valve.

10. The infusion system of claim 1, wherein the catheter is an aspiration catheter.

11. The infusion system of claim 1, wherein the catheter includes a fluid jet emanatory and wherein the constant output of fluid is directed through the fluid jet emanatory.

12. An infusion system, comprising:
an infusion pump including a cylinder having a first end and a second end and a piston disposed within the cylinder, the cylinder having an evacuation chamber, an infusion chamber and a transition section positioned between the evacuation chamber and the infusion chamber; and
a catheter coupled to the infusion pump, and;
wherein the piston separates the evacuation chamber and the infusion chamber;
wherein the piston changes direction at the first end of the cylinder;
wherein the piston reciprocates between the evacuation chamber and the infusion chamber at a piston speed, wherein the piston speed changes such that a constant output is maintained out of the pump;
wherein the piston accelerates from the transition section as the piston approaches the first end of the cylinder;
wherein the piston speed includes a first speed, a second speed, and a third speed;
wherein the first, the second or both the first and second speeds are greater than the third speed;
wherein the piston has a first acceleration from the third speed to the first speed, and wherein the piston has a second acceleration from the third speed to the second speed, and wherein the first acceleration and the second acceleration are configured to provide the constant output of fluid out of the pump.

13. The infusion system of claim 12, wherein a movement of the piston causes a filling of the infusion chamber with fluid while simultaneously evacuating fluid from the evacuation chamber.

14. The infusion system of claim 12, further comprising at least one inlet coupled to the evacuation chamber, and at least one inlet coupled to the infusion chamber, and wherein the transition section spans a distance between the at least one inlet coupled to the evacuation chamber and the at least one inlet coupled to the infusion chamber.

15. The infusion system of claim 14, wherein the at least one inlet coupled to the evacuation chamber and the at least one inlet coupled to the infusion chamber include at least one unidirectional valve.

16. The infusion system of claim 12, wherein the catheter includes a fluid jet emanatory and wherein the constant output of fluid is directed through the fluid jet emanatory.

17. An infusion system, comprising:
a pump including a cylinder having a first end, a second end and a transition region positioned between the first end and the second end, the pump including a piston disposed within the cylinder; the cylinder having a first transition zone and a second transition zone; and
an aspiration catheter coupled to the infusion pump;
wherein the piston speed includes a first speed, a second speed, and a third speed;
wherein the piston accelerates within the first transition zone from the third speed to the first piston speed at a first acceleration;
wherein the piston moves within the second transition zone from the third speed to the second piston speed at a second acceleration;
wherein the piston changes direction at the first end of the cylinder;
wherein the piston accelerates within the first transition zone as the piston approaches the first end of the cylinder; and
wherein the first acceleration and the second acceleration are configured to maintain a constant output of fluid out of the pump.

* * * * *